United States Patent [19]

Mason

[11] Patent Number: 5,643,937
[45] Date of Patent: Jul. 1, 1997

[54] ANTI-SEBORRHOEIC FORMULATION

[76] Inventor: Kenneth Vincent Mason, 22 Kana Crescent, Slack's Creek, Australia, 4127

[21] Appl. No.: 588,792

[22] Filed: Jan. 19, 1996

Related U.S. Application Data

[63] Continuation of Ser. No. 211,706, filed as PCT/AU92/00543, Oct. 12, 1992 published as WO93/07847, Apr. 29, 1993, Pat. No. 5,536,742.

[30] Foreign Application Priority Data

Oct. 15, 1991 [AU] Australia .................................. PK8926

[51] Int. Cl.$^6$ ...................... A61K 31/415; A61K 31/155
[52] U.S. Cl. ........................... 514/399; 514/635; 514/880; 514/881
[58] Field of Search ...................... 514/398, 399, 514/635, 880, 881

[56] References Cited

U.S. PATENT DOCUMENTS 4,472,421  9/1984  Büchel et al. .......................... 514/399

*Primary Examiner*—Kimberly Jordan
*Attorney, Agent, or Firm*—Townsend and Townsend and Crew LLP

[57] ABSTRACT

Sebhorrhoeic skin conditions in dogs are treated by the topical application of the combination of an anti-fungal drug and a topical antiseptic.

3 Claims, 1 Drawing Sheet

5,643,937

ANTI-SEBORRHOEIC FORMULATION

This is a Continuation of application Ser. No. 08/211,706, filed Apr. 14, 1994, now U.S. Pat. No. 5,536,742, which is a 371 of PCT/U92/00543, filed Oct. 12, 1992, published as WO93/07847, Apr. 29, 1993.

FIELD OF THE INVENTION

THIS INVENTION relates to a composition suited to use as an anti-seborrhoeic formulation which can be for the treatment of the clinical disease seborrhoeic dermatitis in animals such as dogs.

BACKGROUND OF THE INVENTION

Seborrhoea is a chronic skin disease that is considered to be a defect in keratinization with increased scale formulation. Dandruff is a mild form. Seborrhoea is divided into three clinical forms. Seborrhoea sicca which is characterised by dry scaling of the skin. Seborrhoea oleosa is characterised by local to diffuse scaling associated with excessive sebum. Seborrhoeic dermatitis is characterised by scaling and greasiness with gross evidence of local or diffuse inflammation. There are breed predilections for Cocker Spaniels, Springer Spaniels, Basset Hounds and, in particular, the most difficult form occurs in West Highland White Terriers. It is considered to be a primary keratinization defect of genetic origin. Although some causes are known, these if found are designated secondary seborrhoeas. Primary idiopathic seborrhoeic dermatitis is currently considered to be a chronic disease that can be ameliorated but not cured.

Standard ameliorating treatments are usually shampoos containing salicylic acid, sulphur, selenium sulphide, tars and antiseptics. These give only very temporary relief from symptoms, usually for a few days at the most.

Human seborrhoeic dermatitis has recently been associated with the yeast *Malassezia (Pityrosporum) ovale*. *Malassezia pachydermaris* has been reported to be associated with a dermatitis in dogs. However, dogs with the classic seborrhoeic dermatitis in West Highland Whites have been treated with ketaconazole tablets orally without producing a reliable cure. Symptoms re-occurred or worsened while on a treatment.

OBJECT OF THE INVENTION

It is an object of the invention to provide an anti-seborrhoeic formulation which is effective against seborrhoeic dermatitis achieving a therapeutic response not known before from standard treatments.

NATURE OF THE INVENTION

The invention achieves its object in provision of a composition for treatment of seborrhoeic skin disease comprising a broad spectrum anti-fungal drug and/or a topical antiseptic.

Preferably the composition is formulated for topical application and it may include a keratolytic/keratoplastic compound.

Preferably the broad spectrum anti-fungal drug is one of the imidazole/triazole group, for example miconazole.

Preferably the topical antiseptic is a phenol-biguanide type such as chlorhexidine, or tricolsan.

Preferably the keratolytic/keratoplastic compound is selenium sulphide.

Preferably the composition is provided in a shampoo base which might be any standard shampoo base and, in particular, a typical anti-dandruff shampoo base is used.

BRIEF DESCRIPTION OF THE DRAWINGS

The invention will now be described with reference to the graph of FIG. 1 which illustrates the results of a trial of a particular composition in accordance with the invention.

PREFERRED EMBODIMENTS

Figure 1:
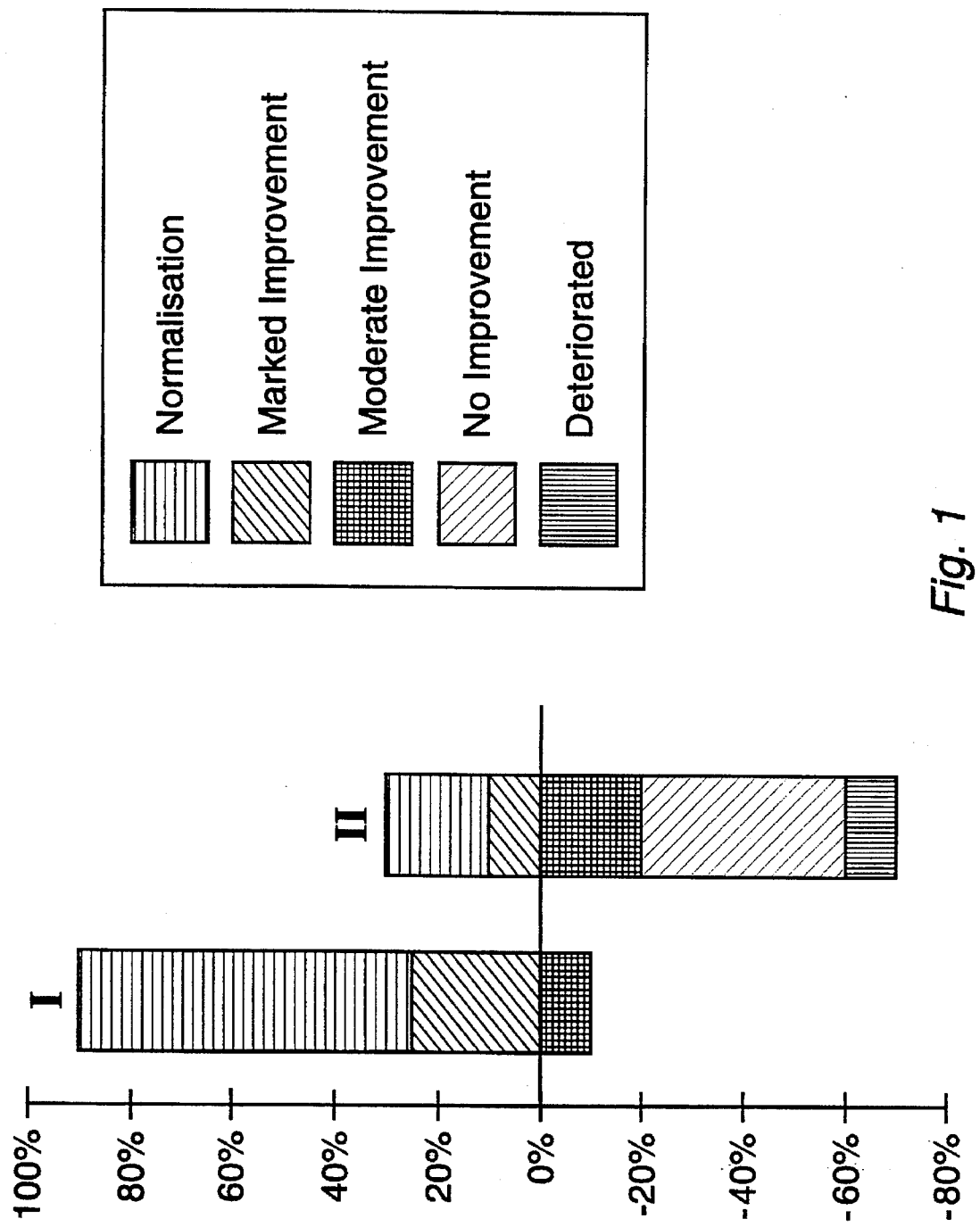

In tests of a composition in accordance with the invention, 41 dogs were diagnosed with seborrhoeic dermatitis. These 41 dogs contained a disproportional high number of West Highland White dogs as compared with the normal dog population. This is to be expected given the breed predisposition to this disease. A double blind randomised clinical trial was designed around two shampoo treatments. Cross over from one treatment group to the other was allowed if the first treatment failed.

The dogs were treated with either an industry standard 1% selenium sulphide shampoo (Selsun Blue or Seleen) originating from Abbots Laboratories or the following composition in accordance with the invention; a shampoo containing 0.25% selenium sulphide, 2.0% chlorhexidine and 2.0% miconazole. All ingredients are measured by weight. The response was then measured on an objective scale by looking for improvement in the clinical symptoms at two and four weeks.

FIG. 1 depicts graphically the results of the trial which indicates that the shampoo combination according to the invention, the graph labeled I, had results far superior to the standard treatment with a 1% selenium sulphide shampoo indicated by the graph labelled II.

Imidazole and Triazole drugs are known potent fungicide chemicals used in medicine and in agriculture. Examples are ketoconazole, miconazole, econazole and enilconazole.

One of the most potent systemic imidazole is ketoconazole. By itself, as a tablet, it has failed to provide a reliable cure in tests on seborrhoeic West Highland White dogs. Partial response in some dogs was followed by recrudescence of the seborrhoea while still on treatment.

Chlorhexidine is a phenol-related biguanide antiseptic, it is a broad spectrum anti-microbial. It has been used as a topical wash, rinse and in a shampoo in veterinary and human medicine for over 30 years. Despite being widely used, it has not gained a reputation for value in seborrhoeic dermatitis.

Selenium sulphide in a shampoo base is widely used as an anti-seborrhoeic and anti-dandruff in man and dogs. However, it gives only temporary relief. It has keratoplastic and keratolytic properties. It thus works by suppressing and breaking up scale.

Various combinations of the above active ingredients have been tried in a shampoo base on dogs with seborrhoeic dermatitis. It has been found that combinations of 1.0% selenium sulphide and 1.0% chlorhexidine; 1.0% selenium sulphide, 1% chlorhexidine and 1.0% miconazole; and 0.25% selenium sulphide, with 2% chlorhexidine and 2.0% miconazole were all much more effective than the standard 1.0% selenium sulphide alone. A 2% shampoo with imidazoles such as ketaconazole, miconazole, econazole and enilconazole also produces useful results. However, the best results have been achieved with the composition described above with reference to FIG. 1.

I claim:

1. A method of treating a sebhorreic skin condition in a dog, said method comprising topically applying to said dog of an anti-fungal drug and a topical antiseptic.

2. A method as claimed in claim 1 wherein the topical antiseptic is a phenol-biguanide type and the broad spectrum anti-fungal drug is one of the imidazole/triazole group.

3. A method as claimed in claim 2 wherein the topical antiseptic is chlorhexidine and the anti-fungal drug is miconazole.

* * * * *